United States Patent [19]

Crawley

[11] Patent Number: 5,001,262
[45] Date of Patent: Mar. 19, 1991

[54] METHOD FOR SYNTHESIZING AN AROMATIC HYDRAZINE COMPOUND

[75] Inventor: Michael W. Crawley, Kingswood, Great Britain

[73] Assignee: Eastman Kodak Company, Rochester, N.Y.

[21] Appl. No.: 371,367

[22] Filed: Jun. 26, 1989

[30] Foreign Application Priority Data

Jul. 26, 1988 [GB] United Kingdom ................. 8817810

[51] Int. Cl.$^5$ ........................................... C07C 243/22
[52] U.S. Cl. .................................................. 564/314
[58] Field of Search ........................................ 564/314

[56] References Cited

PUBLICATIONS

Beck et al. (I), "Jour. Org. Chem.", vol. 39, pp. 1839–1841 (1974).
Beck et al. (II), "Tetrahedron", vol. 34, pp. 2057–2068 (1978).
Montanari et al., "Chem & Ind.", p. 412 (6/19/82).
Houben-Weyl, "Method der Organischen Chemie", vol. 10/2, pp. 244–247 (1967).
Fieger et al., "Reagents for Organic Synthesis", vol. 1, p. 1110 (1970).
Roberts et al., "Organic Chemistry", p. 291 (1964).
Hashem, A. I., *Rev. Roum. Chem.*, 27(3), 429–31 (1982); Chem. Abstr. 98(1) 4356(s).
Hashem, A. I., *Indian J. Chem.*, Sect. B., 20B(12), 1086-7 (1981); Chem. Abstr. 97(3) 22947u.
Yakobsen et al., *J. Org. Chem.*, (USSR), 498(2), 1966.

*Primary Examiner*—Richard L. Raymond
*Attorney, Agent, or Firm*—Robert A. Linn

[57] ABSTRACT

This invention describes a method for synthesizing a polyhaloaromatic hydrazine compound, such as a tetra- or a penta- halophenylhydrazine. Such compounds are useful in the preparation of photographic color couplers.

6 Claims, No Drawings

METHOD FOR SYNTHESIZING AN AROMATIC HYDRAZINE COMPOUND

The invention relates to a method for synthesizing aromatic hydrazines and, in particular, to the synthesis of a polyhalophenylhydrazine compound.

A number of methods are known for making polyhalophenylhydrazines. In a paper by H. Suschitzky et al., J. Chem. Soc. c, (1), 67–74, 1971 there is described a process in which (1) pentachloro-nitrobenzene is reduced with iron filings in hydrochloric acid, (2) the so-formed amine is diazotised and (3) the diazo salt is reduced with stannous chloride. This is a multistep method and when employed on a large scale basic problems are encountered. For example, large volumes of solvent are needed to carry out the reduction with stannous chloride. Without such step the reaction mixture is difficult to stir.

The present invention provides a one-step synthesis which is easy to perform and which provides the desired compounds in good yields. The polyhalophenyl hydrazine compounds produced by the method of this invention are useful in the synthesis of photographic color coupler compounds.

According to the present invention there is provided a method for preparing a 2,3,5,6-tetrahalo- or 2,3,4,5,6-pentahalo-phenylhydrazine compound which comprises reacting the corresponding 1-nitro compound with a hydrazine hydrate in a polar solvent.

The hydrazine compounds which may be prepared by the present method have the structural formula:

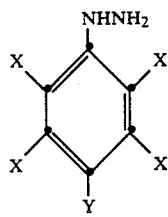

wherein each X is independently Br, Cl or F and Y is hydrogen or as defined for X.

The polar solvent may be dimethylformamide or, preferably, dimethylsulphoxide.

The reaction can take place at ambient temperatures, e.g. between about 15° C. and about 22° C.

Preferably each halogen, X, is chlorine. Other compounds which can be prepared include the following:

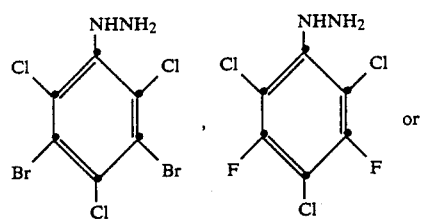

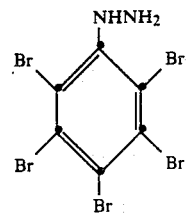

The following examples are included for a better understanding of the invention.

EXAMPLE 1

Preparation of pentachlorophenylhydrazine

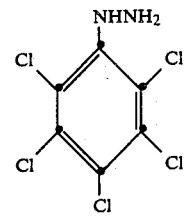

Pentachloronitrobenzene containing 5–10% hexaxchlorobenzene, (3.0 g, 10.1 mmole) was dissolved in dimethylsulphoxide (35 ml). Hydrazine hydrate (1.25 g, 25 mmole) was added dropwise with stirring at 25° C. A slight 4°–5° C. increase in temperature was recorded and the solution became red-brown. After approximately 20 minutes a white solid began to be precipitated. Stirring was continued for one hour after which time TLC (1:1 ethyl acetate: 60°–80° C. petrol) indicated that the reaction was complete. The mixture was poured into stirred water (200 ml) and the solid filtered off and dried at 50° C. overnight. The TLC and IR was identical to an authentic sample of pentachlorophenylhydrazine. Yield=2.27 g, 80%.

EXAMPLE 2

Preparation of 2,3,5,6-tetrachlorophenylhydrazine

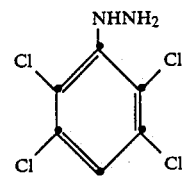

The method of Example 1 was repeated using 2,3,5,6-tetrachloronitrobenzene to provide the product in 81% yield.

The invention has been described in detail with particular reference to preferred embodiments thereof, but it will be understood that variations and modifications can be effected within the spirit and scope of the invention.

I claim:

1. A method of synthesizing a 2,3,5,6-tetrahalo- or 2,3,4,5,6-pentahalophenyl hydrazine which comprises reacting the corresponding 1-nitro compound with 2.5 moles of hydrazine hydrate per mole of 1-nitro compound, in a solvent selected from the class consisting of dimethylformamide and dimethylsulfoxide, and at a temperature of from about 15° to about 22° C.

2. Process of claim 1 wherein said solvent is dimethylsulfoxide.

3. The method according to claim 1 wherein the hydrazine prepared has the formula:

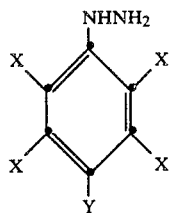

where X is Cl, Br or F and Y is hydrogen or as defined for X.

4. The method according to claim 3 wherein the hydrazine prepared has one of the formulae:

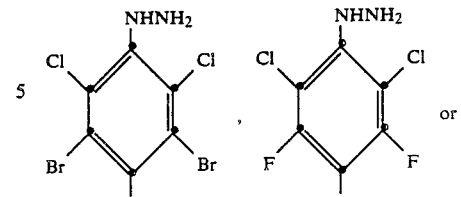

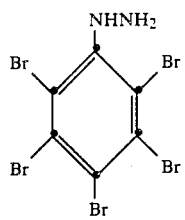

5. Process of claim 1 wherein pentachlorophenylhydrazine is prepared by reacting pentachloronitrobenzene with hydrazine hydrate.

6. Process of claim 1 wherein 2,3,5,6-tetrachlorophenylhydrazine is prepared by reacting 2,3,5,6-tetrachloronitrobenzene with hydrazine hydrate.

* * * * *